(12) United States Patent
Narimatsu et al.

(10) Patent No.: US 6,827,687 B2
(45) Date of Patent: Dec. 7, 2004

(54) BLOOD-PRESSURE MEASURING APPARATUS HAVING WAVEFORM ANALYZING FUNCTION

(75) Inventors: Kiyoyuki Narimatsu, Komaki (JP); Akira Tampo, Komaki (JP); Toshihiko Ogura, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 43 days.

(21) Appl. No.: 10/319,615

(22) Filed: Dec. 16, 2002

(65) Prior Publication Data

US 2003/0199776 A1 Oct. 23, 2003

(30) Foreign Application Priority Data

Apr. 17, 2002 (JP) ........................................ 2002-115186
Sep. 19, 2002 (JP) ........................................ 2002-273914

(51) Int. Cl.[7] .............................................. A61B 5/02
(52) U.S. Cl. .................... 600/485; 600/481; 600/490
(58) Field of Search .......................... 600/481, 485–503

(56) References Cited

U.S. PATENT DOCUMENTS 5,243,990 A * 9/1993 Aung et al. .................. 600/490
5,772,602 A * 6/1998 Sakai et al. .................. 600/495
6,645,156 B2 * 11/2003 Oka ............................ 600/490

FOREIGN PATENT DOCUMENTS

| EP | 0 655 219 A1 | 5/1995 |
| EP | 0 721 764 A2 | 7/1996 |
| EP | 0 824 009 A1 | 2/1998 |
| JP | A 9-140679 | 6/1997 |

* cited by examiner

Primary Examiner—Robert L. Nasser
Assistant Examiner—Patricia C. Mallari
(74) Attorney, Agent, or Firm—Oliff & Berridge, PLC

(57) ABSTRACT

A blood-pressure measuring apparatus including a cuff which is adapted to be worn on a portion of a living subject to press the portion, a waveform analyzing device for analyzing a form of a cuff pulse wave which is obtained from the cuff, and a cuff-pulse-wave obtaining device for obtaining, before the cuff presses the portion of the subject for measuring a blood pressure of the subject, the cuff pulse wave from the cuff so that the waveform analyzing device analyzes the form of the cuff pulse wave.

5 Claims, 11 Drawing Sheets

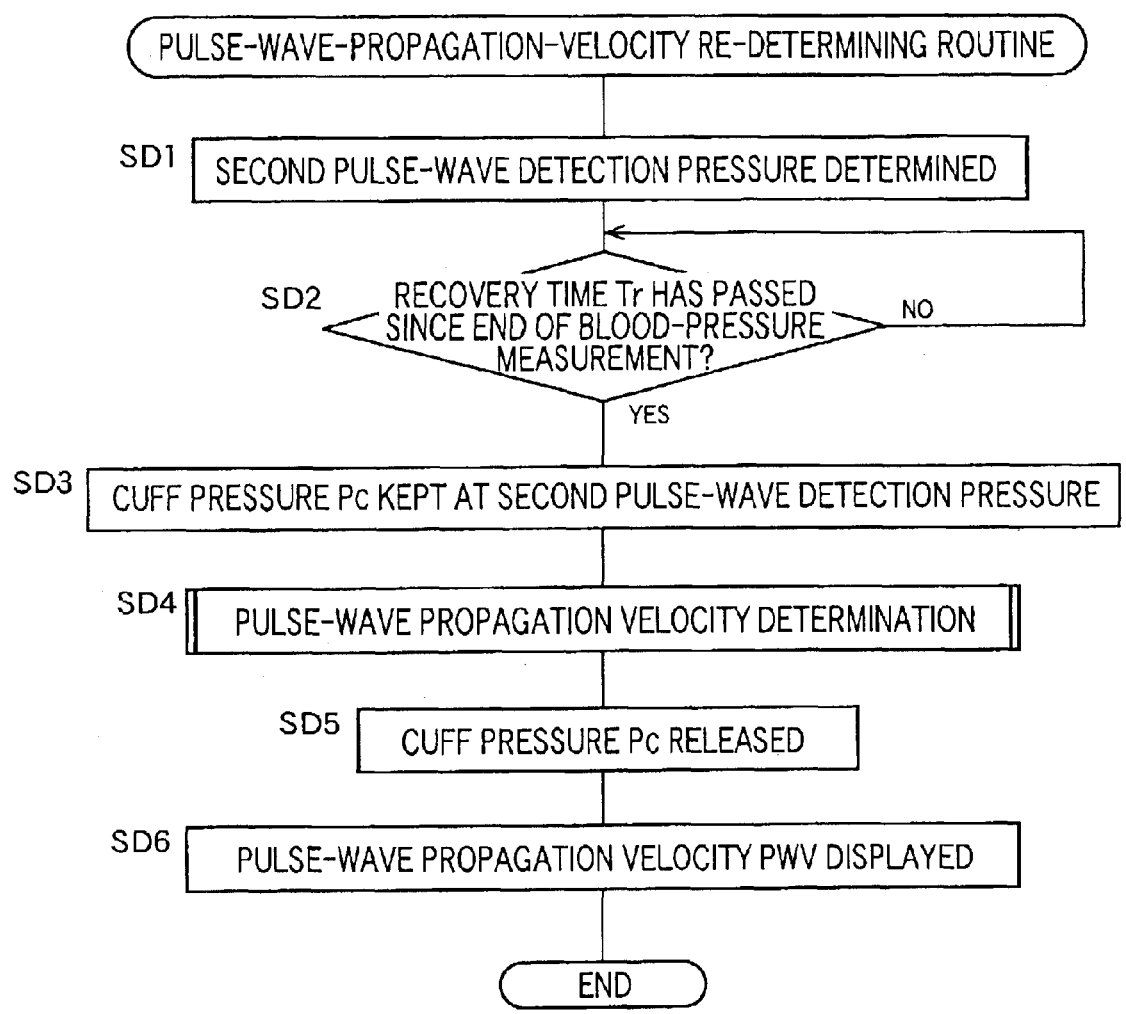

BLOOD-PRESSURE MEASURING APPARATUS HAVING WAVEFORM ANALYZING FUNCTION

BACKGROUND OF THE INVENTION

1. Field of the Invention

The present invention relates to a blood-pressure measuring apparatus having the function of analyzing a shape or form of a pulse wave occurring to a cuff being worn on a living subject. In the present specification, analyzing a waveform means not only analyzing an overall form of a wave but also identifying a specific point on a waveform, such as a peak point or a rising point.

2. Related Art Statement

A blood pressure measurement is carried out by wearing a cuff on a portion of a living subject, such as an upper arm, so as to press the portion, slowly changing a pressure in the cuff, and detecting changes of respective amplitudes of a plurality of heartbeat-synchronous pulses of a pulse wave obtained from the cuff, or detecting Korotkoff sounds, during the changing of the cuff pressure.

The pulse wave obtained from the cuff for the blood-pressure measurement may be utilized such that the form of the cuff pulse wave is analyzed to obtain other sorts of physical information than the blood pressure, such as augmentation index or pulse-wave-propagation-velocity-related information related to a velocity at which the pulse wave propagates in the body of the subject. For example, Japanese Patent Document No. 9-140679 discloses an automatic blood-pressure measuring device having the function of determining a pulse-wave propagation velocity PWV based on a cuff pulse wave.

An augmentation index, generally known as AI, is determined as follows: First, form of cuff pulse wave is analyzed to identify respective peak points of an incident-wave component and a reflected-wave component of the cuff pulse wave. Then, the augmentation index is calculated by dividing a difference between a magnitude of the cuff pulse wave at the time of occurrence of the peak of the incident-wave component and a magnitude of the pulse wave at the time of occurrence of the peak of the reflected-wave component, by a pulse pressure of the pulse wave. Meanwhile, a pulse-wave propagation velocity as a sort of pulse-wave-propagation-velocity-related information is determined as follows: First, form of cuff pulse wave is analyzed to identify a prescribed periodic point on the cuff pulse wave, such as a rising point, a peak point, or a dicrotic notch. Additionally, a heartbeat-synchronous signal detected from a different portion of the subject is analyzed to identify a prescribed periodic point on the heartbeat-synchronous signal. Then, a time difference between the time of detection of the prescribed point of the cuff pulse wave and the time of detection of the prescribed point of the heartbeat-synchronous signal, is determined. Finally, the pulse-wave propagation velocity is calculated by dividing, by the time difference, a propagation distance between the portion where the cuff is worn and the portion where the heartbeat-synchronous signal is detected.

Thus, the cuff worn for carrying out the blood-pressure measurement is utilized to analyze the form of cuff pulse wave and thereby determine the augmentation index or the pulse-wave-propagation-velocity-related information, and accordingly the total number of sensors worn on the subject can be reduced. However, the cuff pulse wave detected from the cuff suffers the problem of low degree of reproducibility or stability. That is, the physical information obtained by analyzing the form of cuff pulse wave cannot enjoy sufficiently high accuracy.

SUMMARY OF THE INVENTION

It is therefore an object of the present invention to provide a blood-pressure measuring apparatus which has, in addition to the function of measuring blood pressure, the function of analyzing the form of a cuff pulse wave for obtaining physical information such as augmentation index or pulse-wave propagation-velocity-related information, and which can detect a cuff pulse wave having an accurate form.

The Inventors have carried out extensive studies to achieve the above object, and have obtained the following knowledge: In many conventional devices in which a cuff pulse wave is detected for blood pressure measurement, the cuff pulse wave detected during the blood pressure measurement is also utilized for obtaining physical information such as pulse-wave propagation velocity. For example, the above-indicated Japanese Patent Document teaches that a cuff pulse wave detected when a pressure in a cuff is slowly decreased after having been increased to a pressure value higher than a systolic blood pressure of a living subject is utilized for determining pulse-wave propagation velocity PWV. However, since the cuff strongly presses a body portion of the subject during the blood pressure measurement, congestion and stopping of venous return, each caused by the pressing of the cuff, and vasodilation caused by abrupt increase of blood-flow amount resulting from the stopping of pressing of the cuff, occurs to the body portion, and accordingly the blood-flow amount or the blood-vessel diameter may change during, or immediately after, the blood pressure measurement. In addition, since respective thickness of skin and subcutaneous tissue of the body portion are decreased once during the measurement and are increased again after the measurement, the respective thickness of skin and subcutaneous tissue may change during a certain time after the measurement. The Inventors have found that since the blood-flow amount, the blood-vessel diameter, and the respective thickness of the skin and subcutaneous tissue affect the shape or form of cuff pulse wave, the reproducibility of cuff pulse wave lowers during, or immediately after, the blood pressure measurement. The present inventions have been developed based on this finding.

The above object has been achieved by the present invention. According to a first aspect of the present invention, there is provided a blood-pressure measuring apparatus comprising a cuff which is adapted to be worn on a portion of a living subject to press the portion; a waveform analyzing means for analyzing a form of a first cuff pulse wave which is obtained from the cuff; and a cuff-pulse-wave obtaining means for obtaining, before the cuff presses the portion of the subject for measuring a blood pressure of the subject, the first cuff pulse wave from the cuff so that the waveform analyzing means analyzes the form of the first cuff pulse wave.

According to this aspect, the cuff-pulse-wave obtaining means obtains, before the cuff presses the portion of the subject for measuring the blood pressure of the subject, the cuff pulse wave from the cuff, for analyzing the form of the cuff pulse wave. Therefore, the cuff pulse wave can be obtained in the state in which the blood-flow amount, blood-vessel diameter, skin, and subcutaneous tissue of the portion of the subject are stable, and accordingly the cuff pulse wave enjoys high accuracy and reproducibility.

A time duration by which the cuff pulse wave is obtained before the pressing of the cuff for the blood pressure measurement may be either short or long. However, in order to minimize the time needed to complete the blood pressure measurement, it is preferred that the time duration be not longer than several seconds.

According to a preferred feature of the first aspect of the present invention, the blood-pressure measuring apparatus further comprises a first pulse-wave-detection-pressure keeping means for keeping, before the cuff presses the portion of the subject for measuring the blood pressure of the subject, a pressure in the cuff to a first pre-determined pulse-wave detection pressure, and the cuff-pulse-wave obtaining means obtains, as the first cuff pulse wave, a pressure oscillation occurring to the cuff in a state in which the pressure in the cuff is kept at the first pre-determined pulse-wave detection pressure.

According to this feature, in the state in which the pressure of the cuff is kept at the pre-determined pulse-wave detection pressure, the cuff pulse wave as the pressure oscillation occurring to the cuff is obtained. Therefore, the cuff pulse wave is free from deformation caused by change of the cuff pressure.

Also, preferably, the pulse-wave detection pressure is pre-determined at a value lower than a diastolic blood pressure of the subject, e.g., in a range of from 40 mmHg to 60 mmHg. Since the pulse-wave detection pressure is lower than the diastolic blood pressure of the subject, the cuff pulse wave is free from deformation caused by tension of the cuff. However, since respective diastolic blood pressure values of living subjects have individual differences, the pre-determined pulse-wave detection pressure may not be appropriate for a particular subject depending upon the diastolic blood pressure of the subject, so that the cuff pulse wave obtained by the cuff-pulse-wave obtaining means may be deformed.

According to another feature of the first aspect of the present invention, the blood-pressure measuring apparatus further comprises a blood-pressure measuring device which measures, using the cuff, a diastolic blood pressure of the subject; a pulse-wave-detection-pressure judging means for judging, based on a comparison between the pre-determined pulse-wave detection pressure and the diastolic blood pressure measured using the cuff, whether the pre-determined pulse-wave detection pressure is appropriate; and a second pulse-wave-detection-pressure keeping means for keeping, when the pulse-wave-detection-pressure judging means judges that the pre-determined pulse-wave detection pressure is not appropriate, the pressure in the cuff to a second pulse-wave detection pressure determined based on the diastolic blood pressure measured using the cuff, after a pre-determined time duration has elapsed since the cuff finished pressing the portion of the subject for measuring the diastolic blood pressure, the time duration being so pre-determined as to allow a tissue of the portion of the subject to recover to a condition thereof before being pressed by the cuff, and the cuff-pulse-wave obtaining means obtains, in a state in which the pressure in the cuff is kept at the second pulse-wave detection pressure by the second pulse-wave-detection-pressure keeping means, a second cuff pulse wave from the cuff so that the waveform analyzing means analyzes a form of the second cuff pulse wave.

According to this feature, when the pulse-wave-detection-pressure judging means judges that the pre-determined pulse-wave detection pressure is not appropriate, the pressure of the cuff is kept to an appropriate, second pulse-wave detection pressure determined based on the actually measured diastolic blood pressure measured and, in this state, another cuff pulse wave is obtained from the cuff for analysis of the form of the cuff pulse wave. Thus, the waveform analyzing means can analyze the form of the cuff pulse wave freed of deformation. In addition, the present apparatus can shorten an average overall measurement time as compared with a second aspect of the present invention, described below, according to which a cuff pulse wave used for waveform analysis is obtained, in each case, after blood pressure measurement.

According to a second aspect of the present invention, there is provided a blood-pressure measuring apparatus comprising a cuff which is adapted to be worn on a portion of a living subject to press the portion; a waveform analyzing means for analyzing a form of a cuff pulse wave which is obtained from the cuff; and a cuff-pulse-wave obtaining means for obtaining, after a pre-determined time duration has elapsed since the cuff finished pressing the portion of the subject for measuring a blood pressure of the subject, the cuff pulse wave from the cuff so that the waveform analyzing means analyzes the form of the cuff pulse wave, the time duration being so pre-determined as to allow a tissue of the portion of the subject to recover to a condition thereof before being pressed by the cuff.

According to this aspect, after the cuff finished pressing the portion of the subject for measuring the blood pressure of the subject and further after the tissue of the portion of the subject has recovered to the condition thereof before being pressed by the cuff, the cuff-pulse-wave obtaining means obtains the cuff pulse wave for analyzing the form of the cuff pulse wave. Therefore, the cuff pulse wave can be obtained in the state in which the blood-flow amount, blood-vessel diameter, skin, and subcutaneous tissue of the portion of the subject are stable, and accordingly the cuff pulse wave enjoys high accuracy and reproducibility.

Like the blood-pressure measuring apparatus according to the first aspect of the invention, the blood-pressure measuring apparatus according to the second aspect of the invention may employ a pre-determined pulse-wave detection pressure at which the pressure of the cuff is kept so that the cuff-pulse-wave obtaining means obtains a cuff pulse wave. However, since the blood-pressure measuring apparatus according to the second aspect obtains the cuff pulse wave after the pressing of the cuff for the blood pressure measurement, it is preferred to determine a pulse-wave detection pressure based on a diastolic blood pressure measured in the blood pressure measurement, and obtain a cuff pulse wave in a state in which the cuff pressure is kept at the thus determined pulse-wave detection pressure.

The waveform analyzing means may comprise means for analyzing the form of the cuff pulse wave so as to determine an augmentation index of the subject, or means for analyzing the form of the cuff pulse wave, so as to determine a characteristic point on the form of the cuff pulse wave and thereby obtain pulse-wave-propagation-velocity-related information that is related to a velocity at which the cuff pulse wave propagates in the subject.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 11 is a flow chart representing a pulse-wave-propagation-velocity re-determining routine executed when a negative judgment is made at Step SB11 of FIG. 9.

DETAILED DESCRIPTION OF PREFERRED EMBODIMENTS

Figure 1:
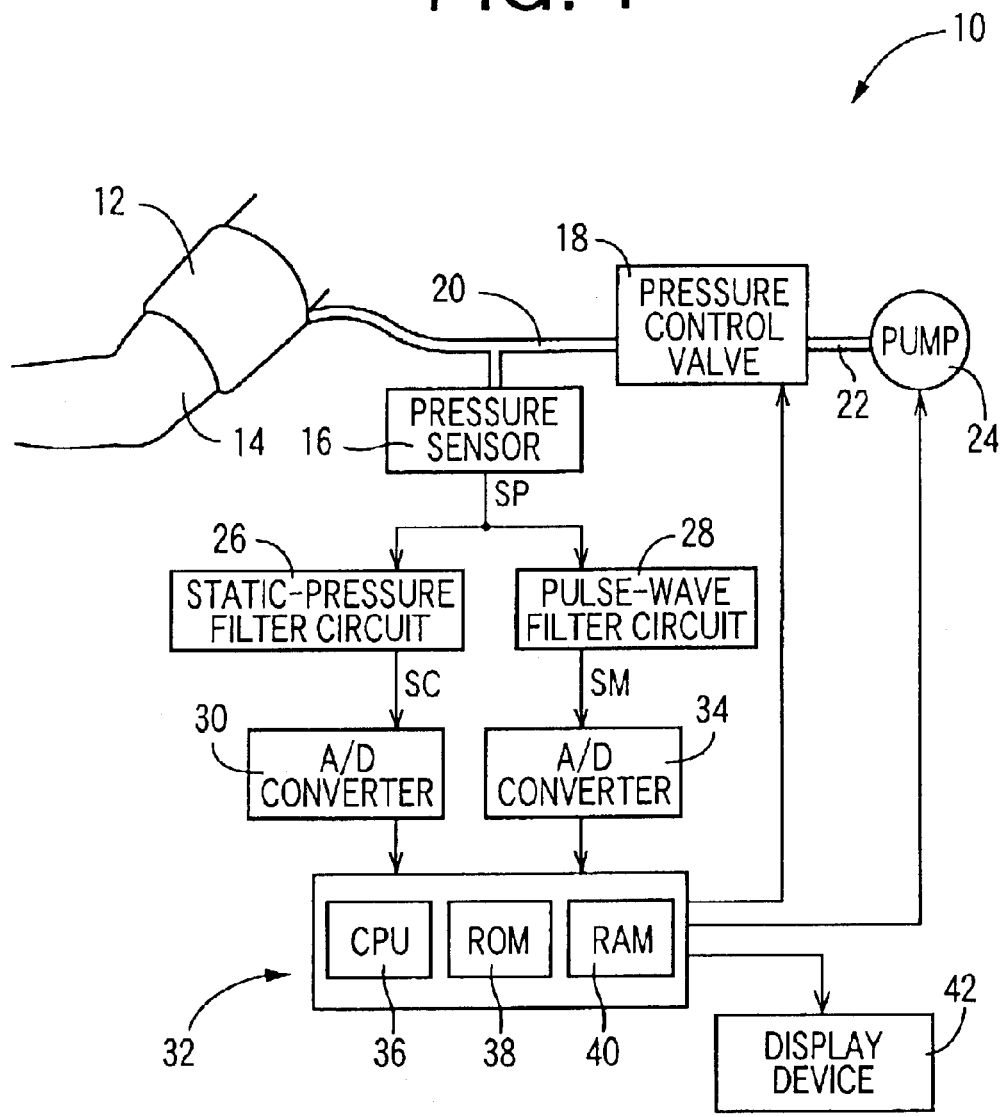
FIG. 1 is a diagrammatic view showing a circuitry of a blood-pressure measuring apparatus which has an augmentation-index determining function as a sort of waveform analyzing function and to which the present invention is applied.

Hereinafter, there will be described an embodiment of the present invention in detail by reference to the drawings. FIG. 1 is a diagrammatic view showing a circuitry of a blood-pressure measuring apparatus 10 to which the present invention is applied and which has an augmentation-index measuring function as a sort of waveform analyzing function. The present blood-pressure measuring apparatus 10 can also be used as an arteriosclerosis inspecting apparatus.

In FIG. 1, reference numeral 12 designates an inflatable cuff which includes a belt-like cloth bag and a rubber bag accommodated in the cloth bag and which is adapted to be wound around an upper portion 14 of a living subject. The cuff 12 is connected via a piping 20 to a pressure sensor 16 and a pressure control valve 18. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal, SP, representing the detected air pressure, to a static-pressure filter circuit 26 and a pulse-wave filter circuit (i.e., a pulse-wave filter device) 28. The static-pressure filter circuit 26 includes a low-pass filter which extracts, from the pressure signal SP, a cuff-pressure signal, SC, representing a static component of the detected air pressure, i.e., a pressing pressure of the cuff 12 (hereinafter, referred to as the cuff pressure, Pc). The filter circuit 26 supplies the cuff-pressure signal SC to an electronic control device 32 via an A/D (analog-to-digital) converter 30. The pulse-wave filter circuit 28 includes a band-pass filter that permits passing of signals having frequencies of from 1 to 30 Hz and thereby extracts, from the pressure signal SP, a cuff-pulse-wave signal, SM, representing a cuff pulse wave as an oscillatory component of the detected air pressure. The filter circuit 28 supplies the cuff-pulse-wave signal SM to the control device 32 via an A/D converter 34. The cuff pulse wave represented by the cuff-pulse-wave signal SM is a pressure oscillation transmitted from an artery of the subject to the cuff 12 and, since this artery is a brachial artery, the cuff pulse wave is a brachial pulse wave.

The control device 32 is provided by a so-called microcomputer including a CPU (central processing unit) 36, a ROM (read only memory) 38, a RAM (random access memory) 40, and an I/O (input-and-output) port, not shown. The CPU 36 processes signals according to the control programs pre-stored in the ROM 38 by utilizing the temporary-storage function of the RAM 40, and supplies drive signals via the I/O port to the air pump 24 and the pressure control valve 18 so as to control the cuff pressure Pc. Moreover, the CPU 36 has various functions shown in detail in FIG. 2 for determining an augmentation index AI of the subject, and controls what is displayed by a display device 42.

Figure 2:
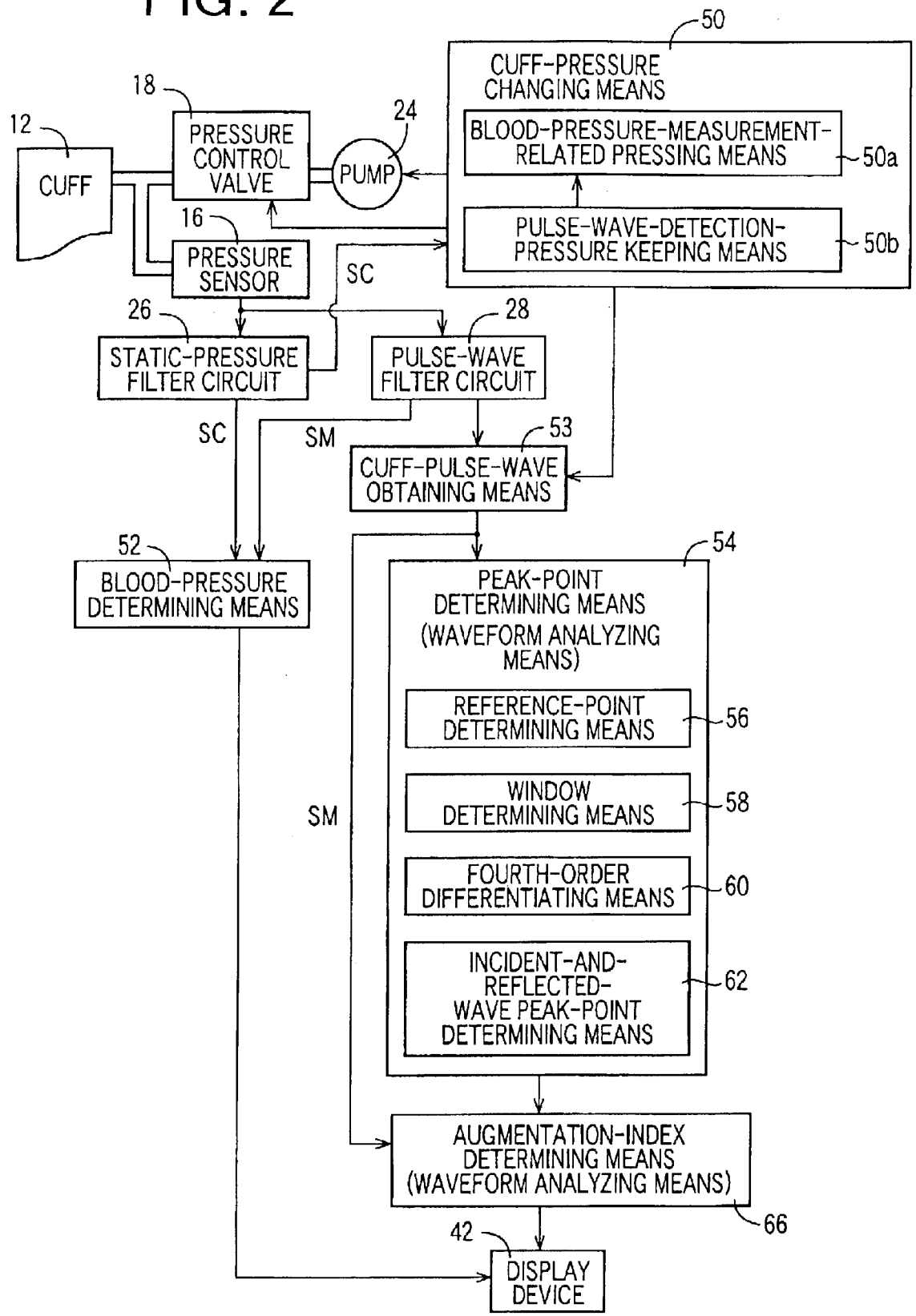
FIG. 2 is a block diagram for explaining essential control functions of an electronic control device of the blood-pressure measuring apparatus having the augmentation-index determining function, shown in FIG. 1.

FIG. 2 is a block diagram for explaining essential control functions of the control device 32 of the blood-pressure measuring apparatus 10.

A cuff-pressure changing means 50 operates, based on the cuff-pressure signal SC supplied from the static-pressure filter circuit 26, the pressure control valve 18 and the air pump 24 so as to change the cuff pressure Pc. Thus, the static-pressure filter circuit 26, the pressure control valve 18, the air pump 24, and the cuff-pressure changing means 50 cooperate with one another to provide a cuff-pressure changing device. The cuff-pressure changing means 50 includes a blood-pressure-measurement-related pressing means 50a for pressing, for a blood-pressure measurement, the upper arm 14 with the cuff 12 being wound, i.e., with a pressure sufficiently higher than a pulse-wave detection pressure, e.g., a pressure higher than a systolic blood pressure $BP_{SYS}$ of the subject; and a pulse-wave-detection-pressure keeping means 50b for keeping, before the pressing of the blood-pressure-measurement-related pressing means 50a for the blood-pressure measurement, the pressure of the cuff 12 to the pulse-wave detection pressure pre-determined to be lower than a diastolic blood pressure $BP_{DIA}$ of the subject, so as to obtain the cuff-pulse-wave signal SM to be used to determine an augmentation index AI. More specifically described, the cuff-pressure changing means 50 keeps, for a time corresponding to not less than one heartbeat of the subject, the cuff pressure Pc to the pre-determined pulse-wave detection pressure lower than the diastolic blood pressure $BP_{DIA}$ of the subject, subsequently quickly increases the cuff pressure Pc from the pulse-wave detection pressure to a target pressure value (e.g., 180 mmHg) pre-determined to be higher than the systolic blood pressure $BP_{SYS}$ of the subject, and then slowly decreases the cuff pressure Pc at a prescribed rate of from 2 to 3 mmHg/sec.

Finally, after a blood-pressure determining means 52, described later, determines a diastolic blood pressure $BP_{DIA}$ of the subject, the cuff-pressure changing means 50 releases the cuff pressure Pc.

If the above-indicated pulse-wave detection pressure is higher than a diastolic blood pressure $BP_{DIA}$ of the subject, the cuff pulse wave extracted by the pulse-wave filter circuit 28 is deformed. In particular, if pulse-wave detection pressure is higher than a mean blood pressure $BP_{MEAN}$ of the subject, the cuff pulse wave is so largely deformed that an accurate augmentation index AI cannot be determined. Thus, the pulse-wave detection pressure is preferably lower than a mean blood pressure $BP_{MEAN}$ of the subject, more preferably lower than a diastolic blood pressure $BP_{DIA}$ of the subject. On the other hand, if the cuff pressure Pc is too low, the cuff pulse wave detected is too small to determine an accurate augmentation index AI. Thus, the pulse-wave detection pressure is pre-determined at a value that assures that a cuff pulse wave having a sufficiently great magnitude is detected, for example, from 40 mmHg to 60 mmHg.

The blood-pressure determining means 52 determines, based on the cuff-pressure signal SC continuously supplied from the static-pressure filter circuit 26, and the change of respective amplitudes of a plurality of heartbeat-synchronous pulses of the cuff-pulse-wave signal SM continuously supplied from the pulse-wave filter circuit 28, each during the slow decreasing of the cuff pressure Pc under the control of the cuff-pressure changing means 50, a systolic blood pressure $BP_{SYS}$, a mean blood pressure $BP_{MEAN}$, and a diastolic blood pressure $BP_{DIA}$ of the subject, according to well-known oscillometric method. In addition, the determining means 52 operates the display device 42 to display the thus determined systolic blood pressure $BP_{SYS}$, etc.

A cuff-pulse-wave obtaining means 53 obtains, before the pressing of the cuff 12 for the blood-pressure measurement, i.e., the pressing of the blood-pressure-measurement-related pressing means 50a, and in the state in which the cuff pressure Pc is kept at the pulse-wave detection pressure by the pulse-wave-detection-pressure keeping means 50b, a length of the cuff-pulse-wave signal SM that corresponds to at least one heartbeat of the subject, for the purpose of determining an augmentation index AI.

Figure 3:
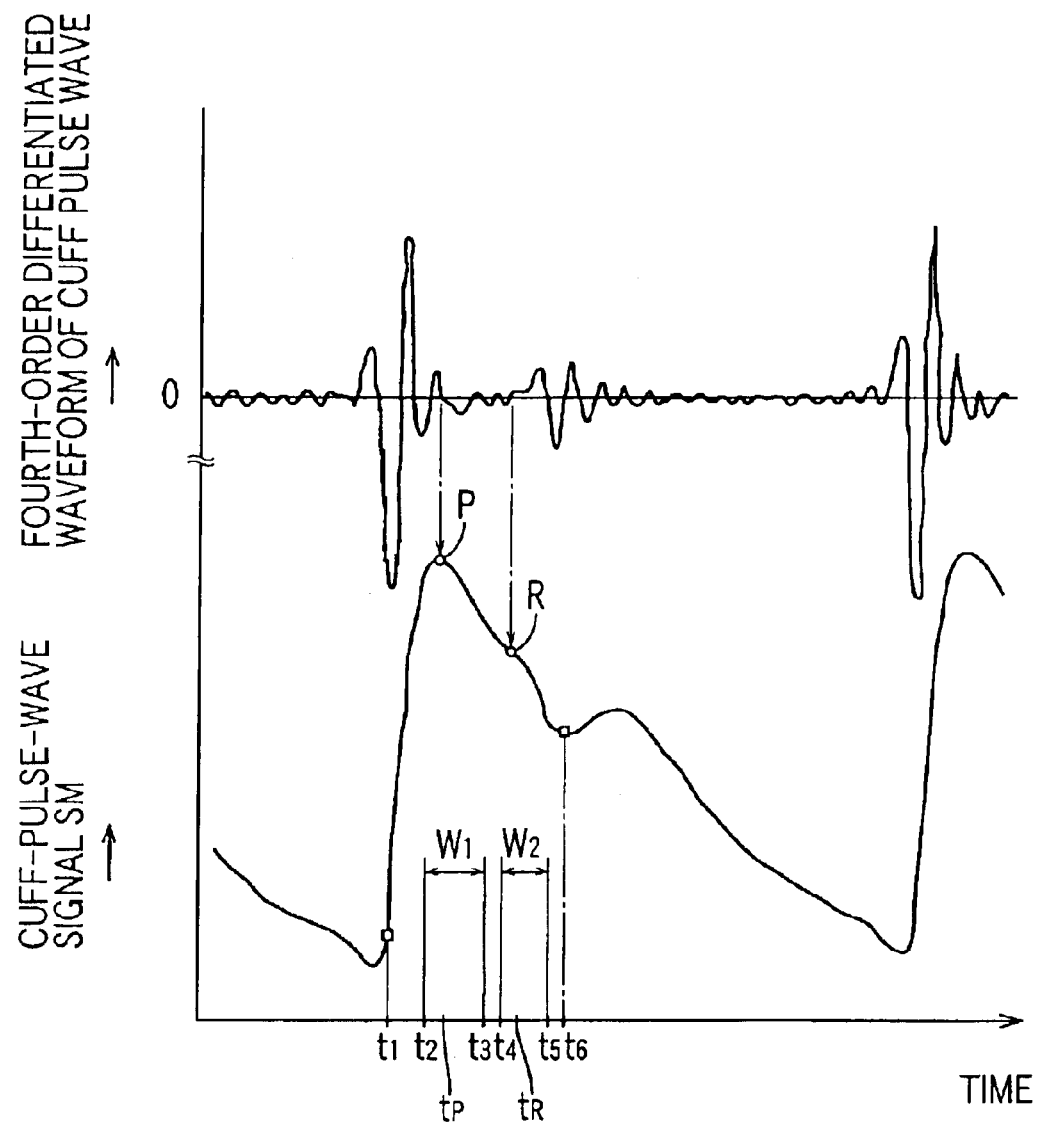
FIG. 3 is a time chart showing a relationship among a cuff pulse wave, a fourth-order-differentiated waveform, a rising-point window W1, a dicrotic-notch window W2, an incident-wave peak point P, and a reflected-wave peak point R that are obtained or determined by the control device shown in FIG. 2.
Figure 4:
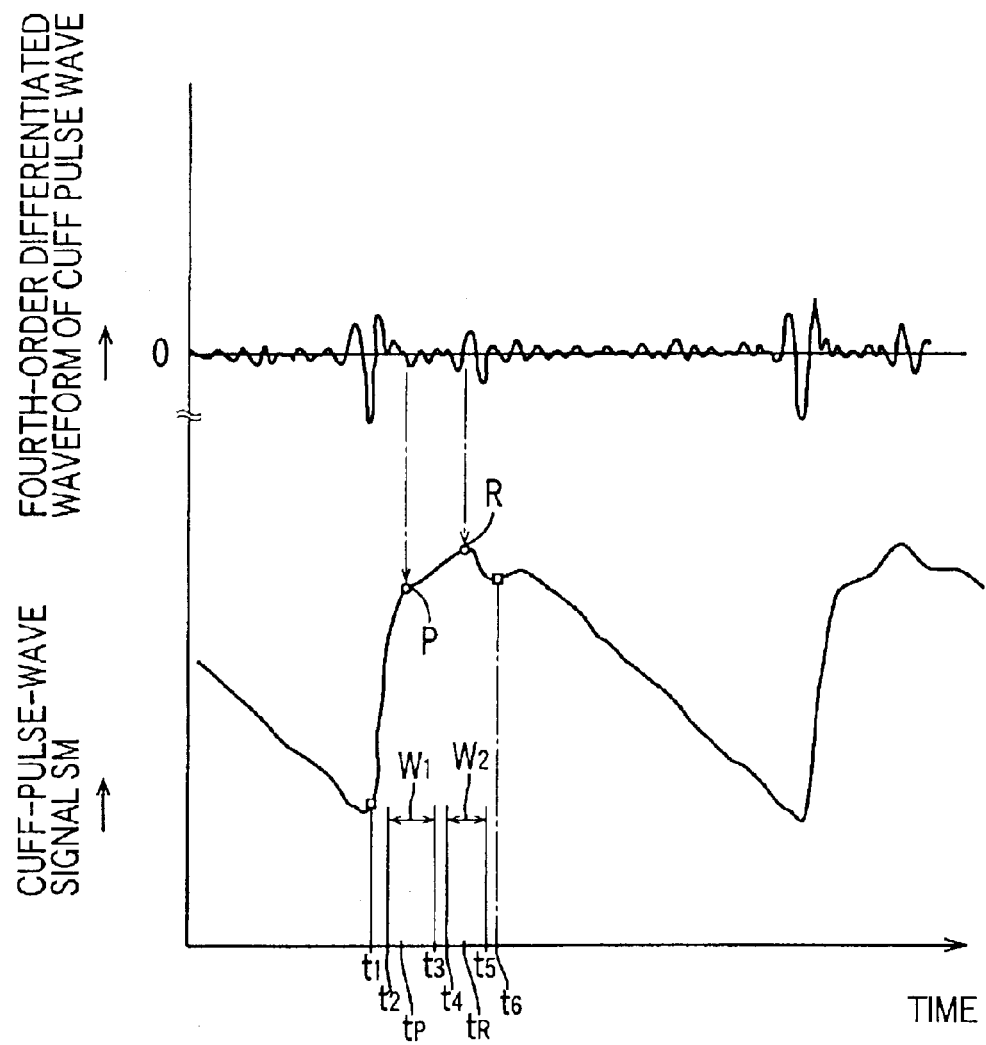
FIG. 4 is a time chart showing a relationship among a cuff pulse wave having a different waveform than that of the cuff pulse wave shown in FIG. 3, a fourth-order-differentiated waveform, a rising-point window W1, a dicrotic-notch window W2, an incident-wave peak point P, and a reflected-wave peak point R.

A peak-point determining means 54 functioning as part of a waveform analyzing means subjects, to fourth-order differentiation (i.e., four-time differentiations), the cuff-pulse-wave signal SM obtained from the cuff 12 by the cuff-pulse-wave obtaining means 53 in the state in which the cuff pressure Pc is kept at the pulse-wave detection pressure, and determines, based on the thus obtained fourth-order-differentiated waveform of the signal SM, more specifically, zero-crossing points of the differentiated waveform, a peak point P of an incident-wave component of the signal SM, a time $t_P$ of occurrence of the point P, a peak point R of a reflected-wave component of the signal SM, and a time $t_R$ of occurrence of the point R. FIGS. 3 and 4 show two cuff-pulse-wave signals SM having different waveforms, respectively, and their respective fourth-order-differentiated waveforms, and each of the FIGS. 3 and 4 shows the corresponding one signal SM and its differentiated waveform along a common time axis, and a peak point P of an incident-wave component of the signal SM, a time $t_P$ of occurrence of the point P, a peak point R of a reflected-wave component of the signal SM, and a time $t_R$ of occurrence of the point R that are determined based on the one signal SM and the differentiated waveform.

The peak-point determining means 54 includes a reference-point determining means 56 for determining, based on the form of the cuff pulse wave obtained by the cuff-pulse-wave obtaining means 53, reference points on the cuff pulse wave, i.e., a rising point $t_1$ and a notch point $t_6$; a window determining means 58 for determining a rising-point window (i.e., a time gate) $W_1$ that starts and ends at a time $t_2$ and a time $t_3$, respectively, that are subsequent by respective prescribed times to the rising point $t_1$, and additionally determining a notch-point window (a time gate) $W_2$ that starts and ends at a time $t_4$ and a time $t_5$, respectively, that are prior by respective prescribed times to the notch point $t_6$; a fourth-order differentiating means 60 for fourth-order differentiating, i.e., four times differentiating the cuff pulse wave obtained by the cuff-pulse-wave obtaining means 53; and an incident-and-reflected-wave peak-point determining means 62 for determining, based on two zero-crossing points of the thus obtained fourth-order differentiated waveform that fall within the rising-point window $W_1$ and the notch-point window $W_2$, respectively, a peak point P of an incident-wave component of the cuff pulse wave, a time $t_P$ of occurrence of the point P, a peak point R of a reflected-wave component of the cuff pulse wave, and a time $t_R$ of occurrence of the point R. The reference-point determining means 56 determines, as a rising point $t_1$, a point that is subsequent to a minimum point of a heartbeat-synchronous pulse of the cuff pulse wave and has a magnitude equal to a predetermined proportion, e.g., one tenth, of an amplitude between the minimum point and a maximum point of the heartbeat-synchronous pulse, and additionally determines, as a notch point $t_6$, the first local minimum point, or the first inflection point, subsequent to the maximum point. The incident-and-reflected-wave peak-point determining means 62 determines, as a peak point $t_P$ of an incident-wave component, a zero-crossing point that has a pre-determined position as counted from the start point of the rising-point window $W_1$, e.g., the first zero-crossing point falling in the rising-point window $W_1$, and crosses zero in a direction from a positive area to a negative area; and additionally determines, as a peak point $t_R$ of a reflected-wave component, a zero-crossing point that has a pre-determined position as counted from the start point of the notch-point window $W_2$, e.g., the first zero-crossing point falling in the notch-point window $W_2$, and crosses zero in a direction from the negative area to the positive area. The respective times from the rising point $t_1$ to the start and end points of the rising-point window $W_1$ and the respective times from the notch point $t_6$ to the start and end points of the notch-point window $W_2$, employed by the window determining means 58, are experimentally determined in advance so that the peak points $t_P$, $t_R$ can fall in the widows $W_1$, $W_2$, respectively.

An augmentation-index determining means 66 functioning as another part of the waveform analyzing means, first determines a maximum magnitude and a minimum magnitude of a heartbeat-synchronous pulse of the cuff pulse wave obtained by the cuff-pulse-wave obtaining means 53, and additionally determines a pulse pressure (i.e., a maximum amplitude) PP as a difference between the maximum and minimum magnitudes. Moreover, the augmentation-index determining means 66 determines, according to a relationship represented by the following Expression 1, an augmentation index AI based on the pulse pressure PP and a difference $\Delta P (=b-a)$ obtained by subtracting a magnitude, a, of the cuff-pulse-wave signal SM at the time of occurrence of peak point $t_P$ of the incident-wave component from a magnitude, b, of the signal SM at the time of occurrence of peak point $t_R$ of the reflected-wave component, and operates the display device 42 to display the thus determined augmentation index AI:

$$AI = (\Delta P/PP) \times 100 \ (\%) \quad \text{(Expression 1)}$$

Figure 5:
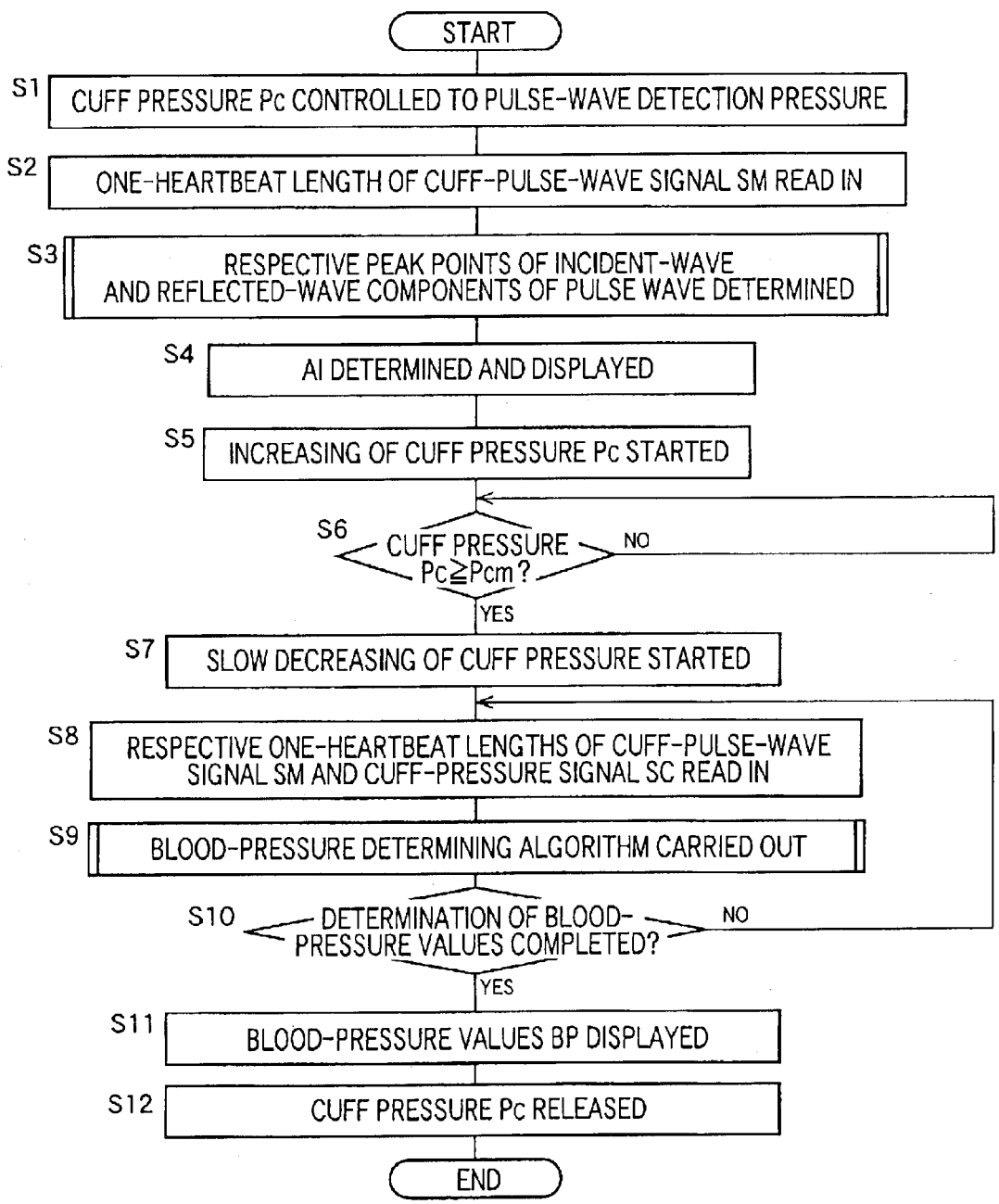
FIG. 5 is a flow chart for explaining the essential control functions of the control device the blood-pressure measuring apparatus having the augmentation-index determining function, shown in FIG. 1.
Figure 6:
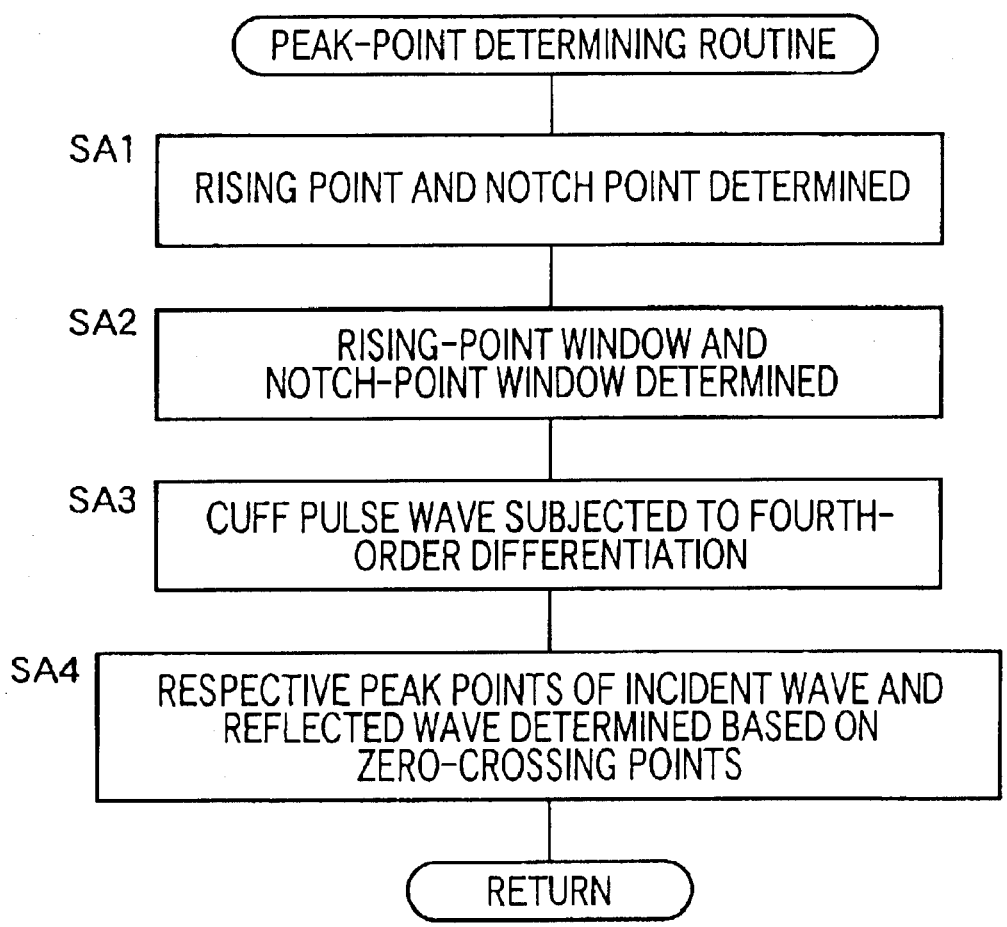
FIG. 6 is a flow chart for explaining a peak-point determining routine employed in the flow chart shown in FIG. 5.

FIG. 5 is a flow chart representing the control functions of the CPU 36, shown in the block diagram of FIG. 2; and FIG. 6 is a flow chart representing a sub-routine corresponding to an incident-and-reflected-wave peak-point determining operation carried out according to FIG. 5.

In FIG. 5, when a measurement starting operation, not shown, is carried out, the control of the CPU starts with Step S1 (hereinafter, the term "Step(s)" is omitted) corresponding to the pulse-wave-detection-pressure keeping means 50b. At S1, the CPU starts the air pump 24 and the pressure control valve 18, and keeps the pressure in the cuff 12 wound around the upper arm 14, to the pulse-wave detection pressure. Subsequently, the control goes to S2 corresponding to the cuff-pulse-wave obtaining means 53. At S2, the CPU reads in a length of the cuff-pulse-wave signal SM that corresponds to at least one heartbeat of the subject. Then, the control goes to S3 corresponding to the peak-point determining means 54. At S3, the CPU carries out the peak-point determining routine shown in FIG. 6.

In FIG. 6, the control of the CPU starts with SA1 corresponding to the reference-point determining means 56. At SA1, the CPU determines, based on the waveform of the cuff pulse wave represented by the cuff-pulse-wave signal SM obtained from the cuff 12 the pressure of which is kept at the pulse-wave detection pressure, reference points on the cuff pulse wave, i.e., a rising point $t_1$ and a notch point $t_6$. For example, the reference-point determining means 56 determines, as the rising point $t_1$, a point that is subsequent to a minimum point of a heartbeat-synchronous pulse of the cuff pulse wave and has a magnitude equal to a predetermined proportion, e.g., one tenth, of an amplitude between the minimum point and a maximum point of the heartbeat-synchronous pulse, and additionally determines, as the notch point $t_6$, the first local minimum point, or the first inflection point, subsequent to the maximum point. Subsequently, the control goes to SA2 corresponding to the window determining means 58. At SA2, the CPU determines a rising-point window (a time gate) $W_1$ that starts and ends at a time $t_2$ and a time $t_3$, respectively, that are subsequent by respective prescribed times to the rising point $t_1$, and additionally determining a notch-point window (a time gate) $W_2$ that starts and ends at a time $t_4$ and a time $t_5$, respectively, that are prior by respective prescribed times to the notch point $t_6$. Subsequently, the control goes to SA3 corresponding to the fourth-order differentiating means 60. At SA3, the CPU subjects, to fourth-order differentiation, the cuff-pulse-wave signal SM obtained from the cuff 12 the pressure of which is kept at the pulse-wave detection pressure. Then, the control goes to SA4 corresponding to the incident-and-reflected-wave peak-point determining means 62. At SA4, the CPU determines, based on two zero-crossing points of the thus obtained fourth-order differentiated waveform that fall within the rising-point window $W_1$ and the notch-point window $W_2$, respectively, a peak point P of an incident-wave component of the cuff-pulse-wave signal SM, a time $t_P$ of occurrence of the point P, a peak point R of a reflected-wave component of the signal SM, and a time $t_R$ of occurrence of the point R.

Back to FIG. 5, after the peak point P of the incident-wave component of the cuff-pulse-wave signal SM, the time $t_P$ of occurrence of the point P, the peak point R of the reflected-wave component of the signal SM, and the time $t_R$ of occurrence of the point R are thus determined, the control goes to S4 corresponding to the augmentation-index determining means 66. At S4, the CPU first determines a pulse pressure (a maximum amplitude) PP of the cuff-pulse-wave signal SM obtained from the cuff 12 the pressure of which is kept at the pulse-wave detection pressure, and then determines a difference $\Delta P$ (=b−a) by subtracting a magnitude, a, of the cuff-pulse-wave signal SM at the time of occurrence of peak point $t_P$ of the incident-wave component from a magnitude, b, of the signal SM at the time of occurrence of peak point $t_R$ of the reflected-wave component. Moreover, the CPU determines, according to the relationship represented by the above-indicated Expression 1, an augmentation index AI based on the pulse pressure PP and the difference $\Delta P$, and operates the display device 42 to display the thus determined augmentation index AI.

After the augmentation index AI is thus determined, the control goes to Steps S5 to S11 for carrying out a blood pressure measurement. More specifically described, at S5, the CPU starts quick increasing of the cuff pressure Pc from the pulse-wave detection pressure to the target pressure value Pcm (e.g., 180 mmHg) determined in advance to be higher than a systolic blood pressure $BP_{SYS}$ of the upper arm of the subject. Then, the control goes to S6 to judge whether the cuff pressure Pc is higher than the target pressure Pcm. S6 is repeated until a positive judgment is made, while the cuff pressure Pc is quickly increased. Meanwhile, if a positive judgment is made at S6, the control goes to S7 to stop the air pump 24 and operate the pressure control valve 18 to slowly decrease the cuff pressure Pc at a low rate of from 3 to 5 mmHg/sec. Thus, S5 to S7 correspond to the blood-pressure-measurement-related pressing means 50a.

Then, at S8, the CPU reads in respective one-heartbeat lengths of the cuff-pulse-wave signal SM supplied from the pulse-wave filter circuit 28 and the cuff-pressure signal SC supplied from the static-pressure filter circuit 26. Subsequently, the control goes to S9 corresponding to the blood-pressure determining means 52. At S9, the CPU determines, based on change of respective amplitudes of a plurality of heartbeat-synchronous pulses of the cuff pulse wave represented by the cuff-pulse-wave signal SM, and respective values of the cuff pressure Pc represented by the cuff-pressure signal SC, each obtained during the slow decreasing of the cuff pressure Pc, a systolic blood pressure $BP_{SYS}$, a mean blood pressure $BP_{MEAN}$, and a diastolic blood pressure $BP_{DIA}$ of the subject, according to well-known oscillometric method. Then, at S10, the CPU judges whether all blood-pressure values BP have been determined at S8. S9 is repeated until a positive judgment is made, while the current blood-pressure measuring operation is continued. Meanwhile, if a positive judgment is made at S10, the control goes to S11 to operate the display device 42 to display the thus determined systolic blood pressure $BP_{SYS}$, mean blood pressure $BP_{MEAN}$, and diastolic blood pressure $BP_{DIA}$ of the subject, determined at S8. Finally, at S12, the CPU operates for releasing the cuff pressure Pc and thereby decreasing the cuff pressure down to atmospheric pressure.

As is apparent from the foregoing description of the present embodiment, the cuff-pulse-wave obtaining means 53 (S2) obtains, before the pressing of the cuff 12 for the blood pressure measurement, the cuff-pulse-wave signal SM to be used to determine the augmentation index AI. Therefore, the cuff pulse wave can be obtained in the state in which the blood-flow amount, the blood-vessel diameter, the skin, and the subcutaneous tissue of the subject are stable, and accordingly the obtained cuff pulse wave enjoys high accuracy and reproducibility. This leads to improving the accuracy of augmentation index AI determined based on the cuff pulse wave.

Also, in the present embodiment, the pulse-wave-detection-pressure keeping means 50b (S1) keeps, before the pressing of the cuff 12 for the blood pressure measurement, the cuff pressure to the pre-determined pulse-wave detection pressure, and the cuff-pulse-wave obtaining means 53 (S2) obtains, in the state in which the cuff pressure is kept, by the pulse-wave-detection-pressure keeping means 50b (S1), to the pre-determined pulse-wave detection pressure, the cuff-pulse-wave signal SM as the pressure oscillation occurring to the cuff 12. Therefore, the cuff pulse wave represented by the signal SM is free from deformation caused by change of the cuff pressure Pc. Thus, the augmentation index AI determined based on the cuff pulse wave enjoys a high accuracy.

Also, in the present embodiment, the pulse-wave-detection-pressure keeping means 50b keeps the cuff pressure to the pulse-wave detection pressure lower than the diastolic blood pressure of the subject, e.g., pressure of from 40 to 60 mmHg. Thus, the cuff-pulse-wave signal SM obtained is free from deformation caused by the tensile force of the cuff 12. Accordingly, the augmentation index AI determined based on the cuff pulse wave enjoys a high accuracy.

Also, in the present embodiment, the blood-pressure-measurement-related pressing means 50a carries out the blood-pressure measuring operation including the slow decreasing of the pressure of the cuff from the value higher than the systolic blood pressure $BP_{SYS}$ of the body portion of the subject where the cuff is worn, to the value lower than the diastolic blood pressure $BP_{DIA}$ of the same. Since the blood-pressure measuring operation is carried out continuously following the cuff-pressure controlling operation carried out by the pulse-wave-detection-pressure keeping means 50b for obtaining the cuff pulse wave to be used to determine the augmentation index, the augmentation index can be determined simultaneously with the determination of blood-pressure values.

Also, in the present embodiment, the blood-pressure measuring apparatus 10 having the augmentation-index determining function can be used as an arteriosclerosis inspecting apparatus. In this case, the arteriosclerosis inspecting apparatus inspects a degree of arteriosclerosis of a living subject based on an augmentation index AI determined by the augmentation-index determining means 66.

Also, in the present embodiment, the peak-point determining means 54 (S3) determines, based on the fourth-order differentiated waveform of the cuff-pulse-wave signal SM, provided by the fourth-order differentiating means 60 (SA3), the respective peak points P, R of the incident-wave and reflected-wave components of the signal SM; and the augmentation-index determining means 66 (S4) accurately determines, as the augmentation index AI, the proportion of the difference AP between the amplitude of the cuff pulse wave at the thus determined peak point P of the incident-wave component and the amplitude of the cuff pulse wave at the thus determined peak point R of the reflected-wave component, to the pulse pressure PP.

Also, in the present embodiment, the reference-point determining means 56 (SA1) determines the rising point of the cuff-pulse-wave signal SM, and the window determining means 58 (SA2) determines the rising-point window $W_1$ based on the rising point of the cuff-pulse-wave signal SM determined by the reference-point determining means 56. In addition, the peak-point determining means 54 determines, based on the zero-crossing point of the fourth-order differentiated waveform that falls in the rising-point window $W_1$, the peak point P of the incident-wave component. Thus, as compared with a case in which a peak point is determined on a moderate waveform, the peak point P of the incident-wave component is more accurately determined and accordingly the augmentation index AI is more accurately determined based on the peak point P.

Also, in the present embodiment, the peak-point determining means 54 selects, as the peak point P of the incident-wave component, one of the zero-crossing points of the fourth-order differentiated waveform that fall in the rising-point window $W_1$, such that the selected one zero-crossing point has prescribed crossing direction and position as seen from the start or end point of the rising-point window $W_1$. Therefore, the peak point P of the incident-wave component is more accurately determined and accordingly the augmentation index AI is more accurately determined based on the peak point P.

Also, in the present embodiment, the reference-point determining means 56 (SA1) determines the notch point of the cuff-pulse-wave signal SM, and the window determining means. 58 (SA2) determines the notch-point window $W_2$ based on the notch point of the cuff-pulse-wave signal SM determined by the reference-point determining means 56. In addition, the peak-point determining means 54 determines, based on the zero-crossing point of the fourth-order differentiated waveform that falls in the notch-point window $W_2$, the peak point R of the reflected-wave component. Thus, as compared with a case in which a peak point is determined on a moderate waveform, the peak point R of the reflected-wave component is more accurately determined and accordingly the augmentation index AI is more accurately determined based on the peak point R.

Also, in the present embodiment, the peak-point determining means 54 selects, as the peak point R of the reflected-wave component, one of the zero-crossing points of the fourth-order differentiated waveform that fall in the notch-point window $W_2$, such that the selected one zero-crossing point has prescribed crossing direction and position as seen from the start or end point of the notch-point window $W_2$. Therefore, the peak point R of the reflected-wave component is more accurately determined and accordingly the augmentation index AI is more accurately determined based on the peak point R.

Next, there will be described another embodiment of the present invention. In the following description, the same reference numerals as used in the above-described first embodiment are used to designate the corresponding elements of the present, second embodiment, and the description thereof is omitted.

Figure 7:
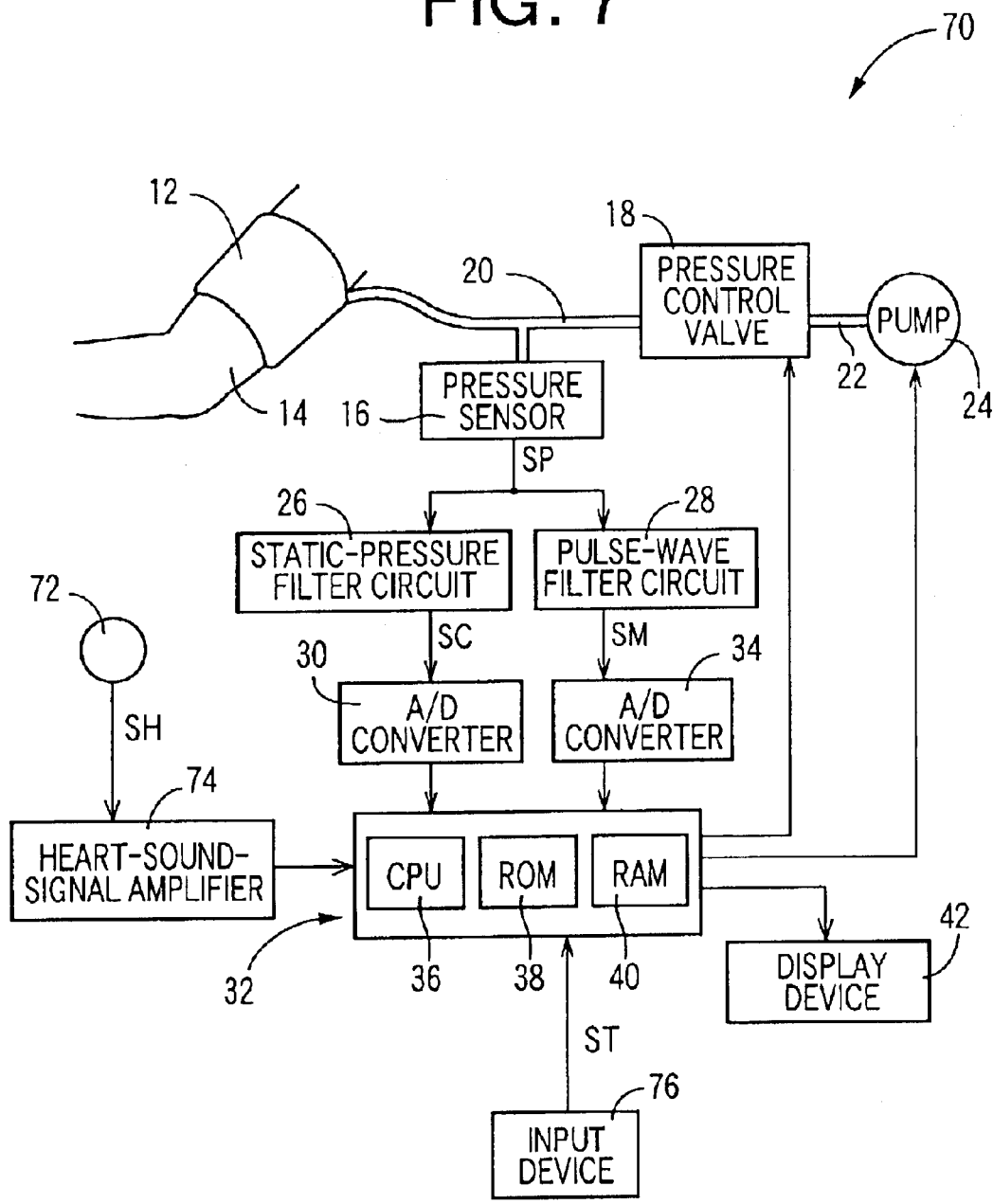
FIG. 7 is a diagrammatic view showing a circuitry of a blood-pressure measuring apparatus which has a waveform-characteristic-point determining function as a sort of waveform analyzing function and to which the present invention is applied, the waveform characteristic point being used for determining pulse-wave propagation velocity PWV.

FIG. 7 is a diagrammatic view for explaining the circuitry of a blood-pressure measuring apparatus 70 having, as the waveform analyzing function, the function of determining, on a waveform, a characteristic point to be used to determine a pulse-wave propagation velocity PWV. The blood-pressure measuring apparatus 70 differs from the blood-pressure measuring apparatus 10 only in that the second apparatus 70 additionally employs a heart-sound microphone 72, a heart-sound-signal amplifier 74, and an input device 76 and that an electronic control device 32 of the second apparatus 70 has different control functions from those of the electronic control device 32 of the first apparatus 10.

The heart-sound microphone 72 is fixed, with an adhesive tape, not shown, to a chest, not shown, of the subject. The heart-sound microphone 72 provides a heartbeat-synchronous-signal detecting device that detects a heart sound as a sort of heartbeat-synchronous signal, and incorporates a piezoelectric element, not shown, that converts a heart sound produced from the subject's heart into an electric signal, i.e., a heart-sound signal SH. The heartsound-signal amplifier 74 includes four sorts of filters that cooperate with one another to attenuate a low-pitch component having a great energy, so that a high-pitch component of the heart sound can be well recorded. The heart-sound-signal amplifier 74 amplifies and filters the heart-sound signal SH supplied from the heart-sound microphone 72, and outputs the amplified and filtered signal SH to the conrol device 32 via an A/D converter, not shown.

The input device 76 includes a plurality of input keys, not shown, that are operable for inputting a stature T of the subject, and supplies a stature signal ST representing the thus inputted subject's stature T to the control device 32.

Figure 8:
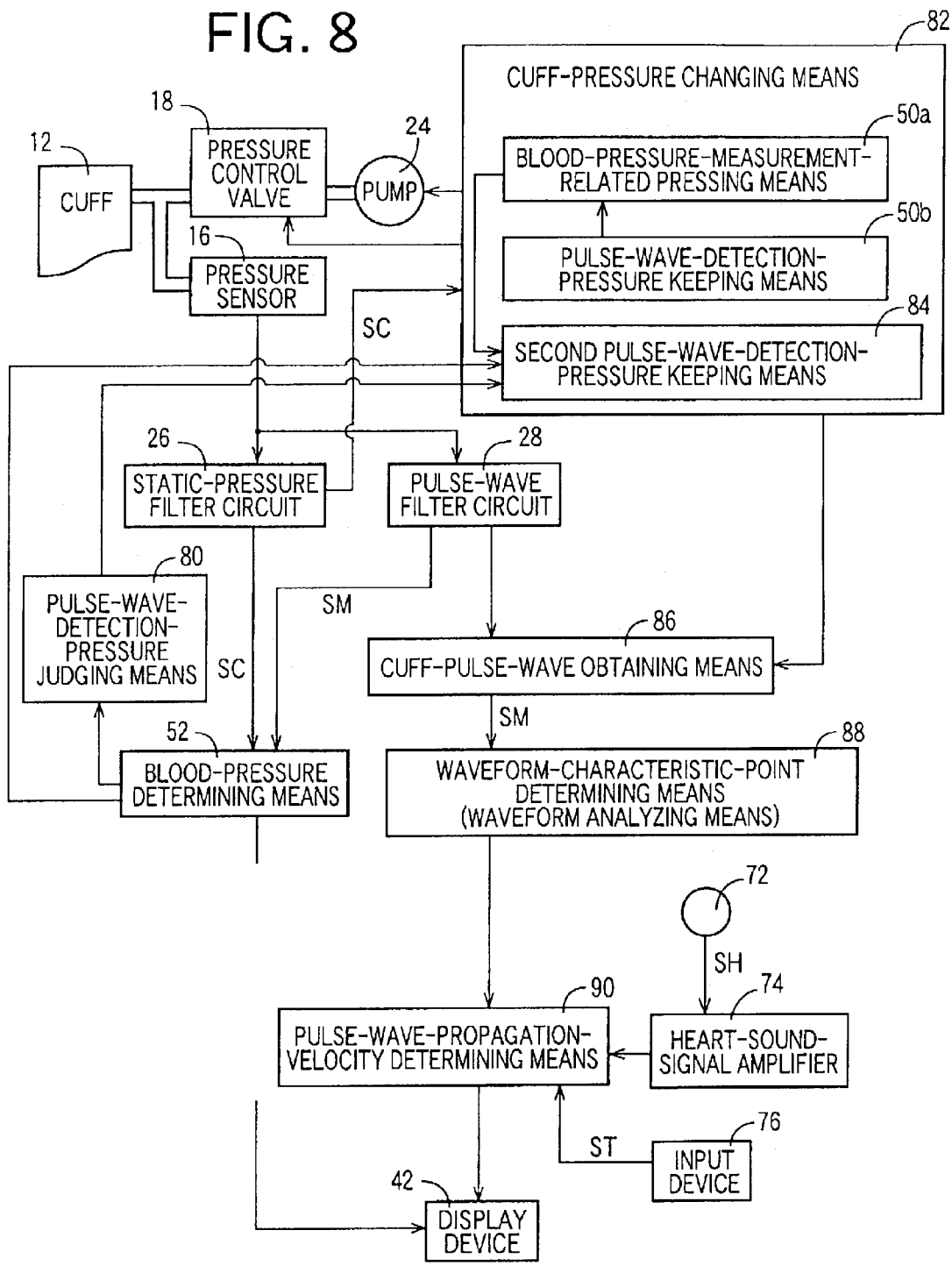
FIG. 8 is a block diagram for explaining essential control functions of a CPU (central processing unit) of the blood-pressure measuring apparatus shown in FIG. 7.

FIG. 8 is a block diagram for explaining essential control functions of a CPU 36 of the blood-pressure measuring apparatus 70.

A pulse-wave-detection-pressure judging means 80 compares a diastolic blood pressure $BP_{DIA}$ of the subject determined by a blood-pressure determining means 52, with a pre-determined pulse-wave detection pressure, and thereby judges whether the pulse-wave detection pressure is appropriate for detecting an accurate cuff pulse wave. As described previously, if the pulse-wave detection pressure is too high as compared with the diastolic blood pressure $BP_{DIA}$, the form of cuff pulse wave is largely deformed; and if the pulse-wave detection pressure is too low as compared with the diastolic blood pressure $BP_{DIA}$, the magnitude of cuff-pulse-wave signal SM is largely decreased. Therefore, the pulse-wave-detection-pressure judging means 80 judges, if the pre-determined pulse-wave detection pressure is too high or too low as compared with the diastolic blood pressure $BP_{DIA}$ determined by the blood-pressure determining means 52, that the pulse-wave detection pressure is not appropriate. The pulse-wave-detection-pressure judging means 80 compares the diastolic blood pressure $BP_{DIA}$ with the pulse-wave detection pressure, in such a manner that first a pressure difference between the diastolic blood pressure $BP_{DIA}$ and the pulse-wave detection pressure is calculated and then it is judged whether the thus calculated pressure difference falls in a range that is experimentally determined in advance.

A cuff-pressure changing means 82 includes, like the cuff-pressure changing means 50, a blood-pressure-measurement-related pressing means 50a and a first pulse-wave-detection-pressure keeping means 50b, and additionally includes a second pulse-wave-detection-pressure keeping means 84.

The second pulse-wave-detection-pressure keeping means 84 determines, if the pulse-wave-detection-pressure judging means 80 judges that the pre-determined pulse-wave detection pressure is not appropriate, a new or second pulse-wave-detection pressure based on the diastolic blood pressure $BP_{DIA}$ of the subject determined by the blood-pressure determining means 52. After a pre-determined recovery time Tr in which the tissue of the body portion around which the cuff is wound recovers to its condition before the pressing of the cuff 12 has passed after the changing of the cuff pressure Pc by the blood-pressure-measurement-related pressing means 50a, the keeping means 84 keeps the cuff pressure Pc to the second pulse-wave detection pressure. This second pulse-wave detection pressure may be determined by subtracting, from the determined diastolic blood pressure $BP_{DIA}$, a pre-determined pressure α, e.g., 10 mmHg. The recovery time Tr may be pre-determined at, e.g., several tens of seconds.

A cuff-pulse-wave obtaining means 86 obtains, like the cuff-pulse-wave obtaining means 53, a length of the cuff-pulse-wave signal SM that corresponds to at least one heartbeat of the subject, before the pressing of the cuff 12 for the blood-pressure measurement, i.e., the pressing of the blood-pressure-measurement-related pressing means 50a, and in the state in which the cuff pressure Pc is kept at the pulse-wave detection pressure by the pulse-wave-detection-pressure keeping means 50b. Also, in the state in which the cuff pressure Pc is kept at the second pulse-wave detection pressure by the second pulse-wave-detection-pressure keeping means 84, the cuff-pulse-wave obtaining means 86 obtains a length of the cuff-pulse-wave signal SM that corresponds to at least one heartbeat of the subject.

A waveform-characteristic-point determining means 88 functioning as a waveform analyzing means determines a characteristic point of the cuff pulse wave obtained by the cuff-pulse-wave obtaining means 86. The characteristic point may be any periodic point on a pulse wave, such as a rising point, peak point, or a notch point.

A pulse-wave-propagation-velocity determining means 90 first determines a time difference between a time of detection of the characteristic point determined by the waveform-characteristic-point determining means 88 and a time of detection of a prescribed point on a heart-sound waveform represented by the heart-sound signal SH supplied by the heart-sound microphone 72. The prescribed point on the heart-sound waveform corresponds to the characteristic point on the cuff pulse wave, and the thus determined time difference means a pulse-wave propagation time DT (sec) by which the pulse wave propagates from the subject's heart to the upper arm 14 where the cuff is worn. In addition, the determining means 90 substitutes the subject's stature T represented by the stature signal ST supplied from the input device 76, for a pre-determined relationship between stature T and propagation distance between subject's heart and upper arm 14, represented by the following Expression 2, so as to determine a propagation distance L, then substitutes the thus obtained propagation distance L and the pulse-wave propagation time DT for the following Expression 3, so as to determine a pulse-wave propagation velocity PWV (cm/sec), and finally operates the display device 42 to display the thus determined pulse-wave propagation velocity PWV:

$$L=aT+b \quad \text{(Expression 2)}$$

where a and b are constants that are experimentally determined.

$$PWV=L/DT \quad \text{(Expression 3)}$$

The waveform-characteristic-point determining means 88 and the pulse-wave-propagation-velocity determining means 90 determine a characteristic point on a cuff pulse wave and a pulse-wave propagation velocity PWV, respectively, with respect to each of a plurality of heartbeat-synchronous pulses of the cuff pulse wave obtained by the cuff-pulse-wave obtaining means 86. Therefore, if the cuff-pulse-wave obtaining means 86 obtains respective lengths of the cuff-pulse-wave signal SM both in the state in which the cuff pressure Pc is kept at the predetermined pulse-wave detection pressure and in the state in which the cuff pressure Pc is kept at the second pulse-wave detection pressure, the determining mean 90 determines a pulse-wave propagation velocity PWV with respect to each of the respective lengths of the cuff-pulse-wave signal SM.

Figure 9:
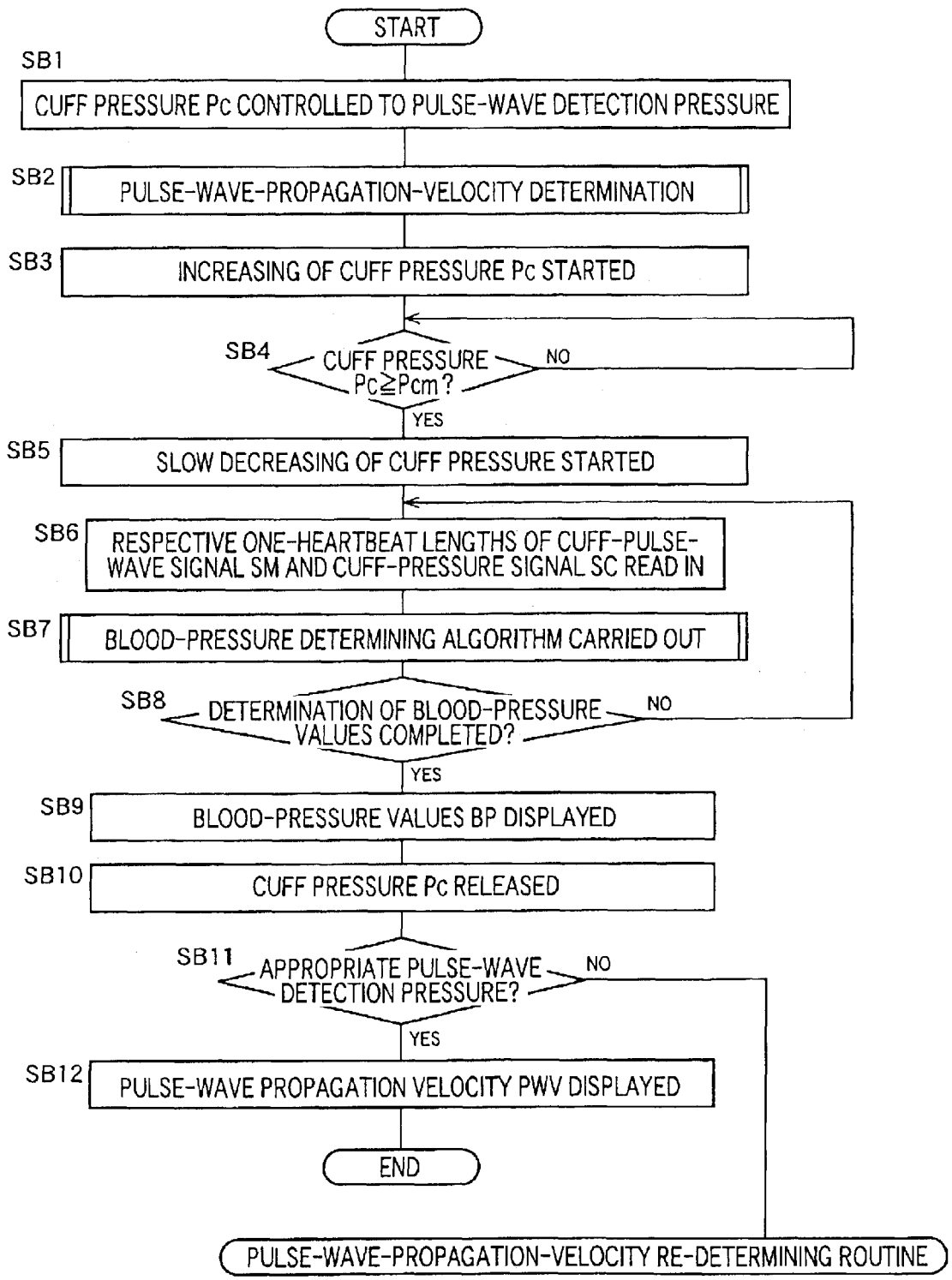
FIG. 9 is a flow chart for more concretely explaining the control functions of the CPU shown in FIG. 8.

FIG. 9 shows a flow chart representing the control functions of the CPU 36, shown in the block diagram of FIG. 8. The flow chart shown in FIG. 9 is started upon operation of a start button, not shown, on an assumption that the stature signal ST has already been supplied to the CPU from the input device 76.

In FIG. 9, SB1 is identical with S1 of FIG. 5, that is, the CPU operates the air pump 24 and the pressure control valve 18 so as to keep the cuff pressure Pc to the pulse-wave detection pressure pre-determined at, e.g., from 40 mmHg to 60 mmHg.

Figure 10:
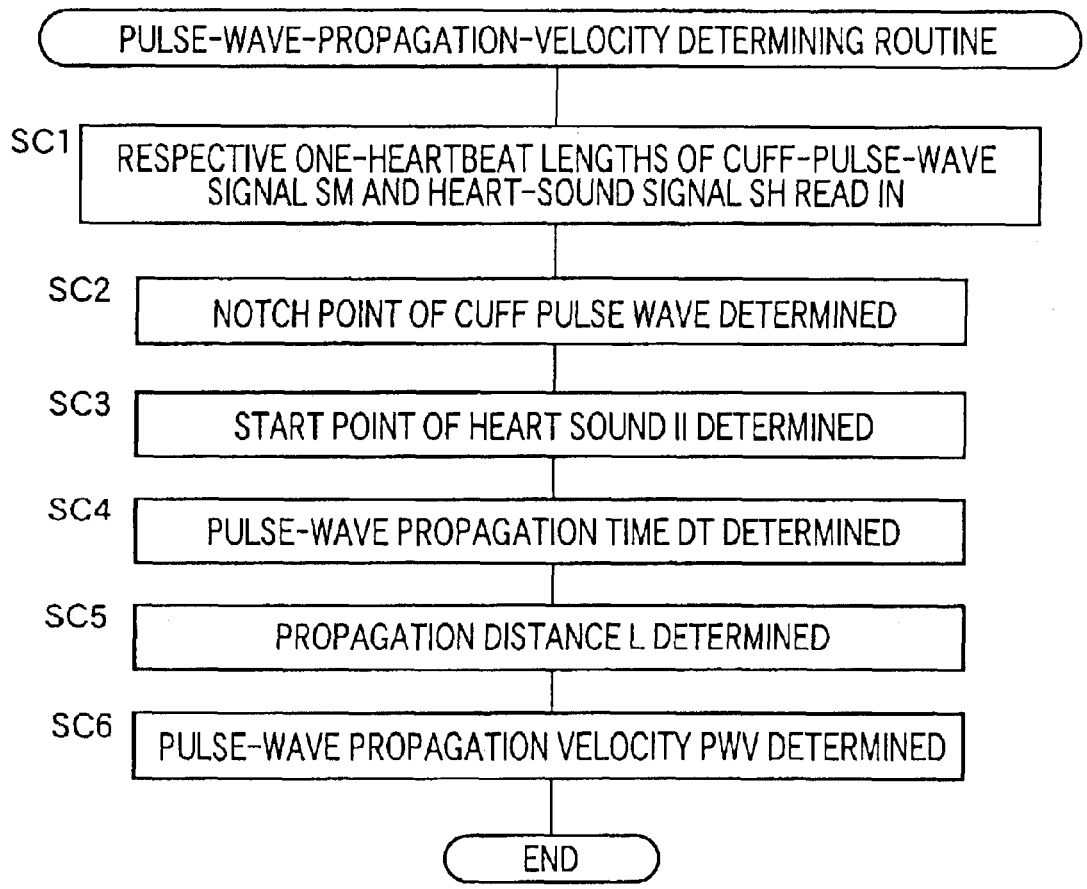
FIG. 10 is a flow chart representing a pulse-wave-propagation-velocity determining routine executed at Step SB2 of FIG. 9 or Step SD4 of FIG. 11.

Then, the control of the CPU goes to SB2, i.e., a pulse-wave-propagation-velocity determining routine shown in FIG. 10. In FIG. 10, at SC1, the CPU reads in respective lengths of the cuff-pulse-wave signal SM and the heart-sound signal SH that correspond to one heartbeat of the subject, in the state in which the cuff pressure Pc is kept at the pre-determined pulse-wave detection pressure.

Subsequently, the control goes to SC2 corresponding to the waveform-characteristic-point determining means 88. At SC2, the CPU analyzes the cuff-pulse-wave signal SM read in at SC1, and thereby determines a notch point as a characteristic point of the signal. For example, the CPU determines, as the notch point, the first local minimum point following the peak point of the heartbeat-synchronous pulse of the cuff pulse wave.

Then, the control goes to SC3 to SC6 corresponding to the pulse-wave-propagation-velocity determining means 90. At SC3, the CPU determines, on the heart-sound waveform represented by the heart-sound signal SH read in at SC1, a start point of a heart sound II that corresponds to the notch point determined at SC2. At SC4, the CPU determines, as a pulse-wave propagation time DT, a time difference between a time of detection of the notch point of the cuff pulse wave determined at SC2 and a time of detection of the start point of the heart sound II determined at SC3.

SC4 is followed by SC5 to substitute, for the above-indicated Expression 2, the subject's stature T represented by the stature signal ST that has already supplied to the control device, and thereby determine a propagation distance L. Then, at SC6, the CPU substitutes the pulse-wave propagation time DT determined at SC4 and the propagation time L determined at SC5, for the above-indicated Expression 3, and thereby determines a pulse-wave propagation velocity PWV. Thus, the present routine is finished.

Back to FIG. 9, SB3 to SB10 are identical with S5 to S12 of FIG. 5 that have already been described above. In short, the cuff pressure Pc is changed, and blood-pressure values BP of the subject are determined during the changing of the cuff pressure Pc.

Then, the control goes to SB11 corresponding to the pulse-wave-detection-pressure judging means 80. At SB11, the CPU calculates a pressure difference by subtracting the diastolic blood pressure $BP_{DIA}$ determined at SB7, from the pre-determined pulse-wave detection pressure and, if the pressure difference falls in a pre-determined range, judges that the pulse-wave detection pressure is appropriate. On the other hand, if not, the CPU judges that the pulse-wave detection pressure is not appropriate. In this case, an upper-limit value of the range is pre-determined at either a negative value, or a positive value which, however, is sufficiently smaller than the pulse-wave detection pressure. Thus, if the pre-determined pulse-wave detection pressure is too high as compared with the diastolic blood pressure $BP_{DIA}$ of the subject, the CPU judges that the pulse-wave detection pressure is not appropriate.

If a positive judgment is made at SB11, the control goes to SB12 to operate the display device 42 to display the pulse-wave propagation velocity PWV determined at SB2. Thus, the present routine is finished. On the other hand, if a negative judgment is made at SB11, the control goes to a pulse-wave-propagation-velocity re-determining routine shown in FIG. 11.

In FIG. 11, SD1 to SD3 correspond to the second pulse-wave-detection-pressure keeping means 84. At SD1, the CPU subtracts, from the diastolic blood pressure $BP_{DIA}$ determined at SB7 of FIG. 9, a pre-determined pressure α, e.g., 10 mmHg, and thereby determines a second pulse-wave detection pressure.

Then, at SD2, the CPU judges whether a recovery time Tr pre-set at, e.g., several tens of seconds, has passed since the end of the blood pressure measurement (i.e., the end of SB10 of FIG. 9). SD2 is repeated until a positive judgment is made. During this recovery time, the blood-flow amount, etc. that have been changed by the pressing of the cuff 12 gradually recover to their initial conditions before the pressing.

Meanwhile, if a positive judgment is made at SD2, the control goes to SD3 to operate the air pump 24 and the pressure control valve 18 so as to keep the cuff pressure Pc to the second pulse-wave detection pressure determined at SD1.

Subsequently, at SD4, the CPU carries out again the pulse-wave-propagation-velocity determining routine of FIG. 10. Thus, the CPU determines a pulse-wave propagation velocity PWV based on the cuff pulse wave obtained in the state in which the cuff pressure Pc is kept at the second pulse-wave detection pressure. In the flow charts shown in FIGS. 9 to 11, SCI of FIG. 10 that is carried out at SB2 of FIG. 9 and SD4 of FIG. 11 corresponds to the cuff-pulse-wave obtaining means 86.

After the pulse-wave propagation velocity PWV is determined at SD4, the control goes to SD5 to operate the air pump 24 and the pressure control valve 18 so as to release the cuff pressure Pc down to an atmospheric pressure. SD5 is followed by SD6 to operate the display device 42 to display the pulse-wave propagation velocity PWV determined at SD4. Thus, the present routine is finished.

As is apparent from the foregoing description of the second embodiment, the second embodiment enjoys the same advantages as those of the first embodiment wherein the cuff-pulse-wave signal SM is obtained for the waveform analysis before the pressing of the cuff 12 for the blood pressure measurement. In addition, if the pulse-wave-detection-pressure judging means 80 (SB11) judges that the pulse-wave detection pressure is not appropriate, the cuff pressure Pc is kept at an appropriate, second pulse-wave detection pressure determined based on the actually measured diastolic blood pressure $BP_{DIA}$ of the subject and, in this state, another cuff pulse wave is obtained for waveform analysis. Therefore, the waveform-characteristic-point determining means 88 (SC2) can determine an accurate characteristic point on the cuff pulse wave less deformed. Thus, an accurate pulse-wave propagation velocity PWV can be determined based on the accurate characteristic point.

While the present invention has been described in its preferred embodiment by reference to the drawings, it is to be understood that the invention may otherwise be embodied.

For example, in each of the illustrated blood pressure measuring apparatuses 10, 70, the cuff 12 is worn the upper arm 14. However, the cuff 12 may be worn on a different body portion of the subject, such as a femoral portion or an ankle.

In each of the illustrated blood pressure measuring apparatuses 10, 70, the cuff pulse wave is obtained in the state in which the cuff pressure Pc is kept at the pre-determined pulse-wave detection pressure. However, a cuff pulse wave may be obtained while the cuff pressure Pc is slowly changed, because a cuff pulse obtained through a high-performance filter is less deformed.

In addition, generally, augmentation index AI is calculated according to the mathematical expression (Expression 1) wherein the denominator is pulse pressure PP. However, even in the case where the denominator is replaced with an amplitude of low-pressure-cuff pulse wave at the time of occurrence of peak point of the incident-wave component or at the time of occurrence of peak point of the reflected-wave component, a value calculated according to the thus modified expression reflects a degree of arteriosclerosis. Therefore, in Expression 1, pulse pressure PP may be replaced with amplitude of low-pressure-cuff pulse wave at the time of occurrence of peak point of the incident-wave component or at the time of occurrence of peak point of the reflected-wave component. In short, augmentation index may be defined as any value that indicates a proportion of a reflected-wave component of a cuff pulse wave to an incident-wave component of the same.

In the first embodiment, the incident-and-reflected-wave peak-point determining means 62 determines, as the peak point P of the incident wave, the first zero-crossing point of the fourth-order differentiated waveform that falls in the rising-point window $W_1$ and where the waveform crosses zero in a direction from a positive area to a negative area, and additionally determines, as the peak point R of the reflected wave, the first zero-crossing point that falls in the notch-point window $W_2$ and where the waveform crosses zero in a direction from the negative area to the positive area. However, the position and direction of each zero crossing may be changed depending upon the manner in which the rising-point window $W_1$ and the notch-point window $W_2$ are determined and the manner in which the fourth-order differentiation is applied to the cuff pulse wave.

In the first embodiment, the peak-point determining means 54 determines the peak point P of the incident wave and the peak point R of the reflected wave, based on the zero-crossing points on the fourth-order differentiated waveform of the cuff-pulse-wave signal SM. However, respective peak points of an incident wave and a reflected wave may be determined on a cuff-pulse-wave signal SM obtained in a state in which the pre-determined pulse-wave detection pressure is higher than a systolic blood pressure $BP_{SYS}$ of a living subject.

In the first embodiment, the augmentation index AI is determined by analysis of waveform and, in the second embodiment, the pulse-wave propagation velocity PWV is determined by analysis of waveform. However, physical information obtained by analysis of waveform is by no means limited. For example, % MAP, i.e., proportion (=100×G/H (%)) of height G of gravity center of area defined by each pulse of cuff pulse wave to height H of peak point of the each pulse, i.e., pulse pressure of the each pulse; or upstroke time, i.e., time from rising point of each pulse of cuff pulse wave to peak point of the each pulse may be determined by analysis of waveform.

In the second embodiment, before pressing of the cuff 12 for blood pressure measurement, a cuff pulse wave is obtained for waveform analysis, in the state in which the cuff pressure Pc is kept at the pre-determined pulse-wave detection pressure and, only in the case where, after the blood pressure measurement, the pulse-wave-detection-pressure judging means 80 judges that the pre-determined pulse-wave detection pressure is not appropriate, the second pulse-wave-detection-pressure keeping means 84 is operated to keep the cuff pressure Pc to the second pulse-wave detection pressure, so that another cuff pulse wave is obtained for the waveform analysis. However, it is possible that no cuff pulse wave be obtained before each blood pressure measurement and the second pulse-wave-detection-pressure keeping means 84 be operated, in each case, to keep the cuff pressure Pc to the second pulse-wave detection pressure, so that after the each blood pressure measurement, a cuff pulse wave is obtained for waveform analysis.

The present invention may be embodied with other changes or improvements that occur to a person skilled in the art without departing from the spirit and scope of the invention.

What is claimed is:

1. A blood-pressure measuring apparatus comprising:

a cuff which is adapted to be worn on a portion of a living subject to press said portion;

a waveform analyzing means for analyzing a form of a first cuff pulse wave which is obtained from the cuff;

a cuff-pulse-wave obtaining means for obtaining, before the cuff presses said portion of the subject for measuring a blood pressure of the subject, the first cuff pulse wave from the cuff so that the waveform analyzing means analyzes the form of the first cuff pulse wave;

a first pulse-wave-detection-pressure keeping means for keeping, before the cuff presses said portion of the subject for measuring the blood pressure of the subject, a pressure in the cuff to a first pre-determined pulse-wave detection pressure;

a blood-pressure measuring device which measures, using the cuff, a diastolic blood pressure of the subject;

a pulse-wave-detection pressure judging means for judging, based on a comparison between the pre-determined pulse-wave detection pressure and the diastolic blood pressure measured using the cuff, whether the pre-determined pulse-wave detection pressure is appropriate; and a second pulse-wave-detection-pressure keeping means for keeping, when the pulse-wave-detection-pressure judging means judges that the pre-determined pulse-wave detection pressure is not appropriate, the pressure in the cuff to a second pulse-wave detection pressure determined based on the diastolic blood pressure measured using the cuff, after a pre-determined time duration has elapsed since the cuff finished pressing said portion of the subject for measuring the diastolic blood pressure, the time duration being so pre-determined as to allow a tissue of said portion of the subject to recover to a condition thereof before being pressed by the cuff;

wherein the cuff-pulse-wave obtaining means obtains, as the first cuff pulse wave, a pressure oscillation occurring to the cuff in a state in which the pressure in the cuff is kept at the first pre-determined pulse-wave detection pressure; and wherein the cuff-pulse-wave obtaining means obtains, in a state in which the pressure in the cuff is kept at the second pulse-wave detection pressure by the second pulse-wave-detection-pressure keeping means, a second cuff pulse wave from the cuff so that the waveform analyzing means analyzes a form of the second cuff pulse wave.

2. A blood-pressure measuring apparatus comprising:

a cuff which is adapted to be worn on a portion of a living subject to press said portion;

a waveform analyzing means for analyzing a form of a cuff pulse wave which is obtained from the cuff; and a cuff-pulse-wave obtaining means for obtaining, after a pre-determined time duration has elapsed since the cuff finished pressing said portion of the subject for measuring a blood pressure of the subject, the cuff pulse wave from the cuff so that the waveform analyzing means analyzes the form of the cuff pulse wave, the timer duration being so pre-determined as to allow a tissue of said portion of the subject to recover to a condition thereof before being pressed by the cuff.

3. An apparatus according to claim 2, further comprising:

a blood-pressure measuring device which measures, using the cuff, a diastolic blood pressure of the subject;

means for determining a pulse-wave detection pressure based on the diastolic blood pressure measured using the cuff; and a pulse-wave-detection-pressure keeping means for keeping the pressure in the cuff to the pulse-wave detection pressure determined based on the diastolic blood pressure measured using the cuff.

4. A blood-pressure measuring apparatus comprising:

a cuff which is adapted to be worn on a portion of a living subject to press said portion;

a waveform analyzing means for analyzing a form of a first cuff pulse wave which is obtained from the cuff; and a cuff-pulse-wave obtaining means for obtaining, before the cuff presses said portion of the subject for measuring a blood pressure of the subject, the first cuff pulse wave from the cuff so that the waveform analyzing means analyzes the form of the first cuff pulse wave;

wherein the waveform analyzing means analyzes the form of the first cuff pulse wave so as to determine an augmentation index of the subject.

5. A blood-pressure measuring apparatus comprising:

a cuff which is adapted to be worn on a portion of a living subject to press said portion;

a waveform analyzing means for analyzing a form of a first cuff pulse wave which is obtained from the cuff; and a cuff-pulse-wave obtaining means for obtaining, before the cuff presses said portion of the subject for measuring a blood pressure of the subject, the first cuff pulse wave from the cuff so that the waveform analyzing means analyzes the form of the first cuff pulse wave;

wherein the waveform analyzing means analyzes the form of the first cuff pulse wave, so as to determine a characteristic point on the form of the first cuff pulse wave and thereby obtain pulse-wave-propagation-velocity-related information that is related to a velocity at which the cuff pulse wave propagates in the subject.

* * * * *